United States Patent
Garbini et al.

(10) Patent No.: US 8,206,305 B2
(45) Date of Patent: *Jun. 26, 2012

(54) MULTI-TWISTED ACOUSTIC ARRAY FOR MEDICAL ULTRASOUND

(75) Inventors: Lex J. Garbini, El Granada, CA (US); Walter T. Wilser, Cupertino, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 588 days.

This patent is subject to a terminal disclaimer.

(21) Appl. No.: 12/237,249

(22) Filed: Sep. 24, 2008

(65) Prior Publication Data

US 2009/0010459 A1 Jan. 8, 2009

Related U.S. Application Data

(63) Continuation-in-part of application No. 11/903,287, filed on Sep. 21, 2007, which is a continuation-in-part of application No. 11/605,738, filed on Nov. 28, 2006.

(51) Int. Cl.
*A61B 8/14* (2006.01)
(52) U.S. Cl. ............ 600/459; 367/61; 367/62; 367/138; 367/160; 29/25.35
(58) Field of Classification Search .................. 600/459; 73/584, 587, 645, 654; 367/61, 62, 72, 138, 367/140, 153–167; 29/25.35
See application file for complete search history.

(56) References Cited

U.S. PATENT DOCUMENTS

| | | |
|---|---|---|
| 4,202,050 A | 5/1980 | Klein |
| 4,515,017 A | 5/1985 | McConaghy |
| 4,567,895 A | 2/1986 | Putzke |
| 5,199,437 A | 4/1993 | Langberg |
| 5,291,893 A | 3/1994 | Slayton |
| 5,388,584 A | 2/1995 | King |
| 5,397,301 A | 3/1995 | Pflueger et al. |
| 5,505,205 A | 4/1996 | Solomon et al. |
| 5,546,946 A | 8/1996 | Souquet |
| 5,680,863 A | 10/1997 | Hossack et al. |
| 5,735,282 A | 4/1998 | Hossack |
| 5,876,345 A | 3/1999 | Eaton et al. |
| 5,916,168 A | 6/1999 | Pedersen et al. |

(Continued)

FOREIGN PATENT DOCUMENTS

WO WO 2006119173 A 11/2006

OTHER PUBLICATIONS

Zagzebski, J.A., Essentials of Ultrasound Physics, Mosby, Inc., 1996. p. 37.*

(Continued)

*Primary Examiner* — Brian Casler
*Assistant Examiner* — Daniel Huntley (57) ABSTRACT

Multiple twisted or rotated arrays are provided. For example, a memory alloy may allow manufacture of multiple rows of elements on a flat substrate. The memory of the alloy is activated to twist different rows in different ways, such as two adjacent substantially parallel but oppositely rotated arrays. By selecting different apertures along a given twist, different planes are scanned due to the difference in direction of the elements of the aperture. By selecting different apertures on differently rotated arrays, a larger volume may be scanned.

20 Claims, 4 Drawing Sheets

U.S. PATENT DOCUMENTS

| | | | |
|---|---|---|---|
| 6,059,731 A * | 5/2000 | Seward et al. | 600/459 |
| 6,126,602 A | 10/2000 | Savord et al. | |
| 6,155,979 A | 12/2000 | Moser | |
| 6,159,153 A | 12/2000 | Dubberstein et al. | |
| 6,447,478 B1 | 9/2002 | Maynard | |
| 6,592,520 B1 | 7/2003 | Peszynski et al. | |
| 6,676,602 B1 | 1/2004 | Barnes et al. | |
| 6,709,396 B2 | 3/2004 | Flesch et al. | |
| 6,795,374 B2 | 9/2004 | Barnes et al. | |
| 6,969,354 B1 | 11/2005 | Marian | |
| 7,497,828 B1 * | 3/2009 | Wilk et al. | 600/443 |
| 7,622,853 B2 | 11/2009 | Rehrig et al. | |
| 2004/0111101 A1 | 6/2004 | Chin | |
| 2004/0158153 A1 | 8/2004 | Hirt et al. | |
| 2006/0173348 A1 | 8/2006 | Wilser et al. | |
| 2007/0066902 A1 | 3/2007 | Wilser et al. | |
| 2008/0125659 A1 | 5/2008 | Wilser et al. | |
| 2008/0125661 A1 | 5/2008 | Garbini et al. | |
| 2008/0287810 A1 | 11/2008 | Park et al. | |

OTHER PUBLICATIONS

Zagzebski, J.A., Essentials of Ultrasound Physics, Mosby, Inc., 1996. p. 37, 60-61.*

Turnbull, DH et al., "Beam Steering with Pulsed Two-Dimensional Transducer Arrays", IEEE Transactions on Ultrasonics, Ferroelectrics and Frequency Control, vol. 38, No. 4, Jul. 1991.

PCT International Search Report, mailed Apr. 22, 2008, 6 pages total.

Bom, et al., *Early and recent intraluminal ultrasound devices*, International Journal of Cardiac Imaging, 1989, pp. 79-88, Kluwer Academic Publishers, Netherlands.

Seward, et al., *Transvascular and Intracardiac Two-Dimensional Echocardiography*, Echocardiography: A Journal of CV Ultrasound & Allied Tech., 1990, vol. 7, No. 4, pp. 457-464.

Schluter, et al. *Transesophageal cross-sectional echocardiography with a phased array transducer system Technique and initial clinical results*, Br Heart F, 1982, vol. 48, pp. 67-72.

Crowley, et al., *Optimized ultrasound imaging catheters for use in the vascular system*, International Journal of Cardiac Imaging 4, 1989, pp. 145-151, Kluwer Academic Publishers, Netherlands.

Valdes-Cruz, et al. *Transvascular Intracardiac Applications of a Miniaturized Phased-Array Ultrasonic Endoscope: Initial Experience With Intracardiac Imaging in Piglets*, Circulation, Mar. 1991, vol. 83, No. 3, pp. 1023-1027.

Crowley, et al., *Ultrasound guided therapeutic catheters: recent developments and clinical results*, International Journal of Cardiac Imaging 6, 1991, pp. 145-156, Kluwer Academic Publishers, Netherlands.

* cited by examiner

MULTI-TWISTED ACOUSTIC ARRAY FOR MEDICAL ULTRASOUND

RELATED APPLICATION

The present patent document is a continuation-in-part of application Ser. No. 11/903,287, filed Sep. 21, 2007, which is a continuation-in-part of application Ser. No. 11/605,738, filed on Nov. 28, 2006, the disclosures of which are hereby incorporated by reference.

BACKGROUND

The present embodiments relate to acoustic arrays for medical ultrasound. Acoustic arrays are formed from semiconductor or piezoelectric material. Piezoelectric materials include solid piezoelectric or composites. The materials transduce between acoustic and electrical energies.

The material is divided into elements, such as dicing a slab of piezoelectric material into a linear array of elements. By mounting on a rigid or semi-rigid backing, the array of elements maintains a desired planar emitting face. The arrangement of elements may be curved for a curved linear array. For example, an array formed from piezoelectric composite material is warped. The elements on the end are positioned away from an azimuth axis. The emitting face of the array is flat in elevation but curved along azimuth.

Two-dimensional arrays are used for three-dimensional imaging. Transducer material is divided into elements along two-dimensions. However, the number of elements becomes large. An alternative is to steer mechanically in one dimension, such as a one-dimensional array in a wobbler transducer. However, the mechanical steering requires space and adds complexity.

Acoustic arrays may be positioned in a catheter, transesophageal probe, or other device for insertion into a patient. Due to the size of the catheter or probe, there may be limited space for conductors or mechanical structures. However, the ability to scan in three-dimensions from a catheter is desired, such as for ablation procedures. For example, U.S. Published Patent Application No. 2006/0173348 shows twisting a one-dimensional array in a catheter for volume imaging. As another example, U.S. Published Patent Application No. 2007/0066902 shows a multidimensional array that is hinged to expand for volume imaging. The hinge may use a memory metal for operation.

Other complex array geometries may be used. However, such arrays may require complex and expensive manufacturing techniques. Fixturing and components with machined parts that match the desired curvature may lead to high cost in materials, tooling, and labor.

BRIEF SUMMARY

By way of introduction, the preferred embodiments described below include methods, systems, improvements, and transducers. Multiple twisted or rotated arrays are provided. For example, a memory alloy may allow manufacture of multiple rows of elements on a flat substrate. The memory of the alloy is activated to twist different rows in different ways, such as two adjacent substantially parallel but oppositely rotated arrays. By selecting different apertures along a given rotated array, different planes are scanned due to the difference in direction of the elements of the aperture. By selecting different apertures on differently rotated arrays, a larger volume may be scanned.

In a first aspect, a system is provided for an acoustic transducer. A first plurality of first elements of a first array define a first emitting face of the first array. The first elements are spaced along an azimuth axis. Some of the first elements of the first array are rotated about the azimuth axis in a twisted relationship relative to other first elements. The first emitting face is angled in different directions based on the rotation. A second plurality of second elements of a second array defines a second emitting face of the second array. The second elements are spaced along an azimuth axis. Some of the second elements of the second array are rotated about the azimuth axis in a twisted relationship relative to other second elements. The second emitting face is angled in different directions based on the rotation. Electrical conductors connect with respective first and second elements.

In a second aspect, a medical ultrasound transducer of elements is provided. The elements are arranged in at least two helices such that different groups of at least one element per group spaced along the azimuth axis of each of the at least two helices are operable to scan different planar regions stacked in elevation and having similar azimuth extent and such that different ones of the planar regions are scanned using different ones of the at least two helices.

In a third aspect, a method is provided for scanning with an acoustic transducer. A first aperture is formed on a first array of elements. The first array of elements is twisted about a first longitudinal axis. A first plane is scanned with the first aperture. A second, different aperture is formed on the first array of elements. The second aperture corresponds to walking the first aperture azimuthally along the first array of elements. The elements of the first array are along a same line defined by the elements being twisted about the first longitudinal axis. A second, different plane is scanned with the second aperture. The position of the second plane corresponds to a different angle of twist associated with the elements of the first aperture than the elements of the second aperture. The forming acts and scanning acts are repeated with a second array of elements twisted about a second longitudinal axis. The repeating is for third and fourth planes different than the first and second planes. A three-dimensional representation is generated as a function of data from the scanning and the relative positions of the first, second, third, and fourth planes.

In a fourth aspect, a method for manufacturing an acoustic array is provided. First and second pluralities of ultrasound elements of the array are connected with a memory alloy. The geometry of the array is altered for the first plurality different than for the second plurality with the memory alloy during manufacture of a transducer probe including the array.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Using a helical array twisted along an azimuth axis, different scan planes may be scanned. By walking an aperture along the azimuth axis, the angles of the acoustic planes vary. A volume may be sampled.

For example, a helical array twists along an azimuth axis. Using a helical array with a large number of elements allows different scan planes to be scanned. By walking an aperture along the azimuth axis, the angles of the acoustic planes vary. A volume may be sampled. The helical geometry and use of such an array are disclosed in U.S. Published Application No. 20080125659 (parent application), the disclosure of which is incorporated herein by reference. The twist is set or permanent, but may be alterable.

The array may be used in ultrasound catheters, transesophageal (TEE) probes, or other transducer for insertion into a patient. The helical array may be used to scan from within a patient. For example, the elevation ends or other portion of the elements lie along a helix (e.g., double helix) where the azimuth centerline is straight. By twisting over a small angle, such as about 28 degrees, a volume may be scanned. By walking the aperture along an axis of the catheter, a volume adjacent to the side of the catheter is scanned. The catheter or other tool is guided using three-dimensional representations generated from the volume scan. The images may assist in guiding for ablation or other procedures.

Shape-memory alloy or superelastic alloy components may be used in ultrasound array fabrication. These alloys provide control over the final array geometry. The superelastic and shape-memory alloys are used to maintain any geometry or to create complex ultrasound array geometries using simple array fabrication techniques.

For example, a shape-memory alloy sheet is affixed to the back of an ultrasound array. The shape-memory alloy may have a helical or a curved shape stored in memory. During array fabrication, the shape-memory sheet is in a flat geometry. The flat geometry greatly simplifies the array manufacturing. During the plastic welding of the subsequent catheter manufacturing or other heat application, the shape-memory alloy reverts to the memorized helical or curved shape. The thermoplastic covering the array is soft enough that the array can assume the geometry defined by the shape-memory alloy. Use of the shape-memory alloy in this way allows the creation of complex array geometries while using the simple array manufacturing methods associated with building planar arrays.

As another example, a superelastic alloy maintains array flatness throughout processing. The superelastic alloy maintains the flatness of a planar array during the ultrasound catheter (or probe) fabrication processes. If the array is twisted, bent or otherwise deformed, the superelastic alloy returns the array to the flat position. The steady state geometry of the superelastic alloy may be non-flat, such as helical. The array and alloy are maintained flat during manufacture, but return to the other geometry of the superelastic alloy once released.

Other arrays may or may not be provided, such as an adjacent untwisted array for two-dimensional imaging. In another embodiment, a mechanical or other structure varies the array between a twisted position and an untwisted position. An untwisted linear array may provide higher resolution two-dimensional imaging than a twisted array. The twisted array may allow for three-dimensional scanning.

To extend the viewing angle for the three-dimensional (3D) or four-dimensional (4D—representing a volume as a function of time) images, an additional array may be provided. For example, one linear array with a helical geometry may allow scanning over 21 degrees by selecting different apertures. Providing multiple helical array sections allows a greater viewing angle. The 21-degree viewing angle may be increased to approximately 84 degrees by using four helical arrays (i.e., a 4× helical array). generated.

Depending on the amount of space, different numbers of helical arrays may be provided. For example, one or two such arrays are used in a catheter, but 3, 4, or more such arrays are used in a TEE probe. Multiple helical arrays may have fewer elements than a two-dimensional array, reducing cost and increasing simplicity. Each section of the array is twisted parallel to the axis of the transducer. By using a portion of each array section and walking these apertures along the catheter axis, a wide-angle 3D/4D volume can be scanned.

The array geometry may be created using any methods, such as a mold. In one embodiment, a shape-memory alloy member within (or in contact with) the ultrasound imaging array provides the geometry including different twisted arrays. The shape-memory alloy may allow precise formation of complex array geometries after the array has been fabricated in the easy-to-manufacture planar form. The multi-twist shape memory sheet may provide precise relative placement of each array section where the array sections are attached to each other through the shape-memory sheet.

A single shape-memory sheet with multiple adjacent alternating right and left hand twists may allow for a greater viewing angle than a single-twist device. To accomplish a wide viewing angle with a single twist device would require a very high twist angle. A single-twist acoustic array with a high viewing angle (high twist) may not hold together due to excessive internal stress. Also, the multi-twist device may provide higher resolution than a single-twist device for the same viewing angle.

Figure 13:
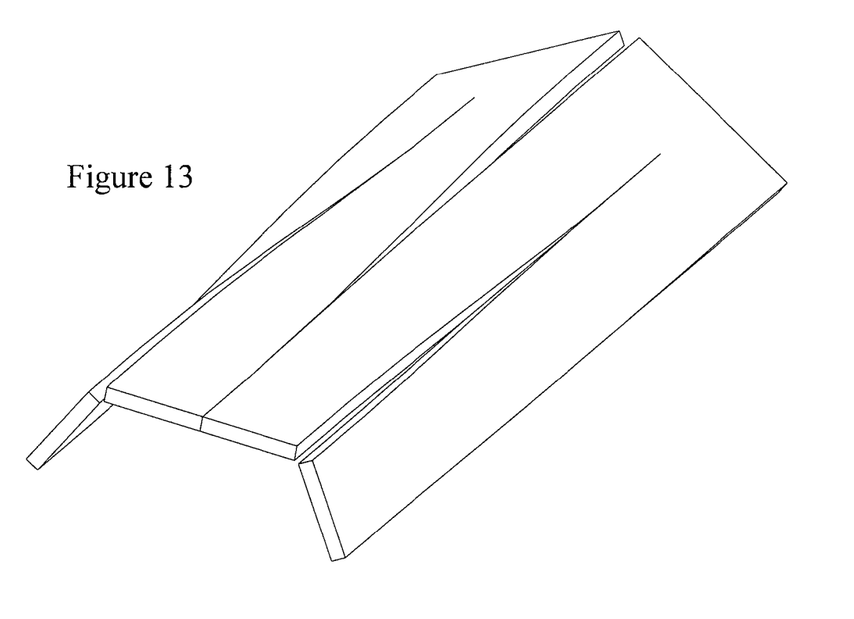
FIG. 13 is a graphical representation of a multiple twisted array memory alloy.

FIGS. 1-12 are provided below with respect to providing one helix. A single linear array is twisted. Alternatively, an array with a plurality of rows is twisted, providing two adjacent helices with similar rotations. FIG. 13 shows one embodiment with multiple different rotations. The FIG. 13 embodiment may use any of the embodiments described for FIGS. 1-12 for one or more of the plurality of twisted arrays.

Figures 1, 2, 4:
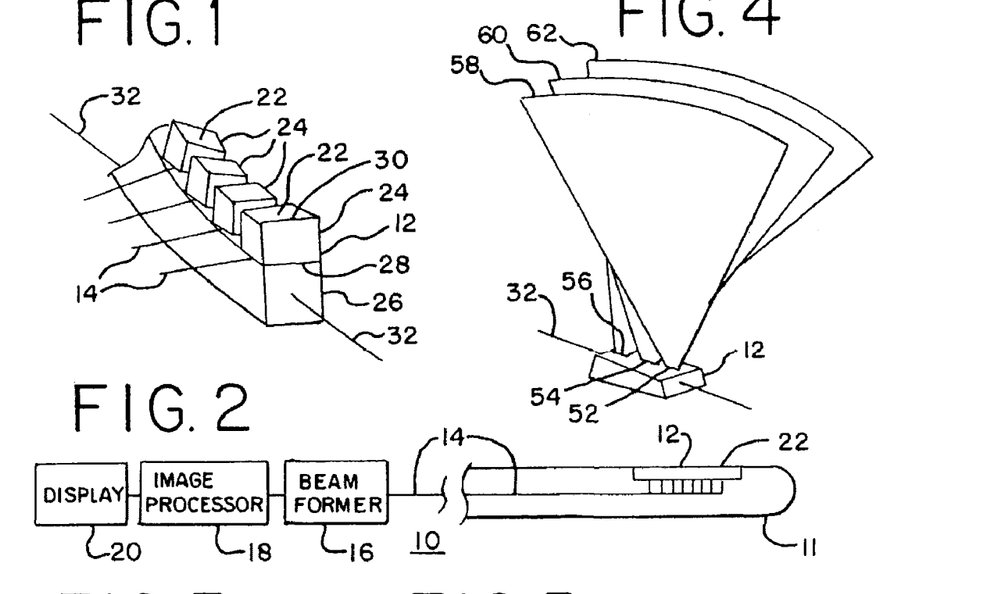
FIG. 1 is a graphical representation of one embodiment of a portion of a helical transducer array.
FIG. 2 is a graphical representation of the array of FIG. 1 in a catheter.
FIG. 4 is a graphical representation of one embodiment of three-dimensional scanning with the array of FIG. 1.

FIGS. 1 and 2 show a system 10 for an acoustic transducer array 12. The system 10 includes the array 12, conductors 14, a beamformer 16, an image processor 18, and a display 20. Additional, different, or fewer components may be provided. For example, the system 10 includes the array 12 and conductors 14 without the beamformer 16, image processor 18, and/or display 20. These imaging electronics may be in a separate ultrasound imaging system. The transducer releasably connects with the imaging system.

The array 12 is used in a transducer probe, such as a medical ultrasound transducer. The transducer probe is used outside of a patient, such as a handheld transducer probe. Alternatively, the transducer is used within a patient, such as a catheter 11 (shown in FIG. 2), a transesophageal, vaginal, intercavity, intraoperative, or other probe. The array 12 and conductors 14 are connected with or positioned in the transducer probe. A window or lens is over the array 12 for acoustic scanning from an emitting face 22 of the array from within the probe.

The array 12 has a plurality of elements 24, backing material 26, electrodes 28, and matching layers 30. Additional, different, or fewer components may be provided. For example, two or more matching layers 30 are used. As another example, a chamber is provided instead of backing material 26. The backing material 26 absorbs acoustic energy to limit or prevent reflections received from a back of the array 12. The matching layers 30 provide a more gradual transition between acoustic impedance, minimizing reflection from the boundary between the transducer and the patient. The electrodes 28 interact with the elements to transduce between acoustic and electrical energy. The variation of potential or distance between electrodes 28 across an element causes electrical signal generation or acoustic energy, respectively.

The elements 24 contain piezoelectric material. Solid or composite piezoelectric materials may be used. Each element is a rectangular solid, cubic, or six sided, but other surfaces may be provided. For example, the emitting face 22 of one or more elements 24 is concave or convex for elevation focusing or frequency based directivity. Alternatively, a microelectromechanical or capacitive device, such as a flexible membrane, is used. Any now known or later developed ultrasound transducer may be used. Longer elements in elevation as compared to wavelength may provide increased elevation directivity.

Any number of elements 24 may be provided, such as 64 elements, 128 elements or other number of elements 24 may allow for more or larger apertures. The elements 24 are adjacent each other, such as having substantially wavelength or less spacing between the centers of adjacent elements 24. For example, the elements 24 have half wavelength spacing with kerfs acoustically separating each element 24. Other methods of element separation may be used. The wavelength spacing is based on a center, average, imaging or other frequency of operation of the array 12. Sparse arrays 12 with greater spacing between elements 24 may be used.

The elements 24 are positioned along an azimuth axis 32. For a one-dimensional array 12, the elements 24 are in a single row along the azimuth axis 32. Thirty-two, fifty or more, sixty-four, one hundred and twenty eight or other numbers of elements 24 may be used. The array 12 may be linear or curved linear. A curved linear array 12 has ends or a middle that extend towards or away from the azimuth axis 32, but the elements 24 are still positioned along the azimuth dimension. Due to the curve, some elements 24 of the array 12 are at different depths or ranges.

Multi-dimensional arrays 12 may be used. For example, two or more rows of elements 24 are adjacent to each other along the elevation dimension. 1.25, 1.5, 1.75 or 2D arrays may be provided. The spacing between elements 24 along the elevation dimension is the same or different than along the azimuth dimension, such as a 2×64 array with half wavelength spacing between all adjacent elements in azimuth. The elements are long in elevation, such as having a 3-20 wavelength elevation width, but may be half wavelength or have other spacing.

The side of the elements 24 covered by the matching layer 30, closer to the region to be scanned, and/or opposite the backing material 26 is the emitting face 22. Acoustic energy is transmitted from and received at the emitting face 22 of the array 12. The angle of acoustic energy relative to the emitting face 22 affects the sensitivity of the elements 24 to the energy. The elements 24 are more sensitive to the energy at normal incidence to the elements 24.

Referring to FIG. 1, some of the elements 24 of the array 12 are rotated. The rotation is about the azimuth axis 32. The azimuth axis 32 extends through the backing material 26, the elements 24, the emitting face 30, or adjacent to the array 12. The rotation forms a helical or spiral pattern of the elements 24. The adjacent elements 24 are arranged in a helix along the azimuth axis 32. One element 24 is rotated by a different amount about the axis 32 than other elements 24. The angle of greatest sensitivity is different for the rotated element 24 as compared to for another element 24, with respect to a particular target. The rotation about the azimuth axis 32 may be in addition to rotation away from the axis 32, such as associated with a curved array.

Each element 24 is rotated by a different amount. For example, the elements 24 at opposite ends of the array 12 are rotated about the azimuth axis by at least 10, at least 15 or other greater or lesser number of degrees relative to each other. The azimuth centerline is straight or may rotate or twist. Greater or lesser total rotation may be used. Each of the elements 24 in between are rotated a different amount to step the rotation between the ends. For example, each element 24 rotates 0.47 degrees as compared to an adjacent element 24 (e.g., 64 elements 24 with 30 degrees total rotation provide 0.47 degrees per element 24). Alternatively, groups of elements 24 are rotated a same amount relative to another element 24 or group of elements 24. For example, half the array 12 is rotated one amount and the other half another amount. Any number of steps may be used, with symmetrical or asymmetrical groupings of elements 12. For example, a center group of elements 24, periodic group of elements 24 or other arrangement of elements 24 face a same direction, but other elements are rotated. In one embodiment, a center half of the elements 24 (e.g., center 64 elements 24) are straight or have a same rotational orientation about the azimuth axis, but one quarter of the elements 24 on each end (e.g., 32 elements 24 on one end and 32 elements 24 on the other end) are rotated in a spiral. The rotation is a single step or a plurality of steps.

Due to the rotation of the elements 24, the emitting face 22 is angled in different directions. The emitting face 22 is twisted, such as associated with a helix with or without an offset from the axis of rotation. The emitting face 22 is rotated in correspondence with the rotation of the elements 24, such as being rotated about the azimuth axis by at least 10 degrees. The emitting face 22 may be twisted more in one area than another. The twist allows for different apertures along the array 12 to have different angles of optimal sensitivity, defining different scanning planes in rotation about the azimuth axis (e.g., different elevation scanning planes).

In general, a larger aperture in elevation provides increased elevation directivity and narrower elevation beamwidth. By twisting the array in elevation, a sub-aperture of elements is used in concert to form an image plane. The total number of independent beams that can be formed by an array is on the order of the number of elements of an aperture. By varying the total twist relative to the elements angular beamwidth, there is a tradeoff between resolution in azimuth and the elevation angular width of the volume formed.

Material holds the elements 24 in the rotated position. For example, the backing material 26 is cured to position the elements 24. As another example, a frame holds the elements 24 in place. In another example, epoxy or other bonding agent cures against a portion or the entire array 12 to hold the array 12 in position. Other materials and associated structures may be used. For the catheter embodiment, the body of the catheter 11 may twist or rotate to avoid interference with, hold in place or assist in holding in place the rotated elements 24.

The backing material 26, electrodes 28, ground plane, and/or matching layers 30 are deformable, allowing twisting with the elements 24. For example, an array normally used as a linear array may be twisted without further changes in manufacture processes. Alternatively, one or more of these layers are formed after twisting to avoid deformation.

The electrical conductors 14 are cables, coaxial cables, traces, wires, flex circuits, wire jumpers, combinations thereof, or other now known or later developed conductor. The conductors 14 electrically connect the electrodes 28 of the array 12 with a connector of the transducer probe or the beamformer 16 (FIG. 2). One or more conductors 14 are provided for each element 24. Alternatively, fewer conductor 14 than elements 24 may be used, such as for switched apertures, partial beamforming, or multiplexing. The conductors 14 are separately addressable. Each element 24 may be selectively used for a given aperture and associated electronic steering. Alternatively, some elements 24 are useable with only a subset of possible apertures.

In one embodiment, the array 12 is positioned within a catheter 11. The array 12 may fit within a 10 French, 3.33 mm, or other diameter catheter 11. The conductors 14 are routed through the catheter 11 to the beamformer 16. The catheter transducer is used for imaging. The images assist in diagnosis, catheter or tool guidance, and/or therapy placement. The geometry may assist in imaging. For example, maintenance of the array 12 as flat or curved with the catheter 11 may reduce imaging artifacts and/or allow sector scanning. By including the helical array 12 within the catheter 11, three-dimensional scanning and image representations may be used. Alternatively, the rotated elements 24 of the array 12 are used in other transducers.

The beamformer 16 includes a plurality of channels for generating transmit waveforms and/or receiving signals. Relative delays and/or apodization focus the transmit waveforms or received signals for forming beams. The beamformer 16 connects with the conductors 14. The beamformer 16 selects an aperture including one, some, or all of the elements 24 of the array 12. Different apertures may be used at different times. The aperture is formed by using the elements 24 for transmit and/or receive operations while not using other elements. The beamformer 16 is operable to scan from a plurality of apertures formed by adjacent groups of the elements 24. The apertures may walk through regular increments or skip to different portions of the array 12.

For scanning, the beamformer 16 electronically focuses along the azimuth direction. A plurality of scan lines using an aperture is scanned. During receive operations, the focus may vary as a function of depth. An elevation focus is provided by a lens and/or element sensitivity, or the array 12 is not focused in elevation. In alternative embodiments, the beamformer 16 connects with elevation spaced elements for at least partial electric focusing and/or steering in the elevation dimension.

In the helical geometry embodiment, different planes are scanned by scanning from different apertures of the array 12. The rotation of the elements 24 positions the scan planes for different apertures at different amounts of rotation about the azimuth axis. Short sections of the array 12, on average, point in different directions offset from sections of the array 12 on either side. For example, the first eight elements 24 of an aperture formed on an array 12 with a total rotation of 32 degrees over sixty four elements 24 rotated by sixty four steps have an angle of −14 degrees. The non-coplanar scan planes of the sequence of eight sequential apertures of eight elements each are at angles of −10, −6, −2, +2, +6, +10 and +14. These eight apertures define eight diverging planes spaced apart in elevation. The diverging planes are stacked adjacent to each other to scan the volume. Using different apertures with some or all elements 24 not in common allows for scanning different planes or regions.

The size of each aperture may be limited by the amount of twist. The useable directivity of the elements 24 within an aperture should overlap, such as overlapping the elevation directivity of the elements 24 at the ends of each aperture. Elevation spaced elements, such as two rows of elements, may allow less twist with electronic assisted steering in elevation to reduce beam spreading and allow longer apertures.

The image processor 18 is a detector, filter, processor, application specific integrated circuit, field programmable gate array, digital signal processor, control processor, scan converter, three-dimensional image processor, graphics processing unit, analog circuit, digital circuit, or combinations thereof. The image processor 18 receives beamformed data and generates images on the display 20. The images are associated with a two-dimensional scan.

Alternatively or additionally, the images are three-dimensional representations. Data representing a volume is acquired by scanning. The processor 18 generates a three-dimensional data set as a function of the scanning by the beamformer. The data of the three-dimensional data set may be interpolated to a Cartesian grid or maintained in a scan format. The relative position of the planes used for scanning may be known or assumed based on the aperture position and rotation of the corresponding elements 24. Any rendering may be used, such as projection, volume, and/or surface rendering. The processor 18 generates the three-dimensional representation from the data representing the volume.

A volume scan may be obtained with the array 12 having a helical geometry. By using the twist of the emitting face 22 of the array 12, different planes within a volume may be scanned. The planes are spaced apart in the elevation dimension, such as extending at different amounts of rotation from the array 12. By electric steering in azimuth, the scans may cover a similar region or have similar extents in the azimuth-range dimension. Alternatively, the array 12 is curved or flat without twist. A volume may be scanned by movement of the array 12 and/or the catheter 12. In other embodiments, a multidimensional array 12 or an array with concave or convex elements allows electronic or frequency steering, respectively, to scan a volume.

Figure 3:
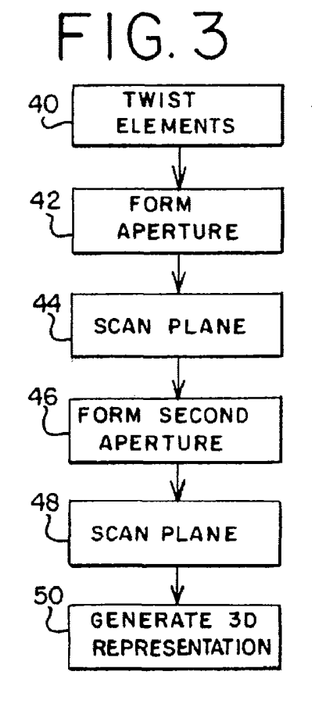
FIG. 3 is a flow chart diagram of one embodiment of a method for scanning with a twisted acoustic array.

FIG. 3 shows a method for scanning with an acoustic array. The method uses the system 10 and/or array 12 of FIGS. 1 and/or 2, or a different array and/or system. Additional, different, or fewer acts may be provided. For example, data representing a volume may be used without generating a three-dimensional representation in act 50. The acts are performed in the order shown, but may be performed in other orders.

In act 40, elements of the array are twisted about a longitudinal axis of the array (i.e., the azimuth axis). The array is twisted into a helix or spiral around the longitudinal axis. The twisting is performed by rotation of the ends of the array, formation of the array in the twisted position, and/or rotation of elements or groups of elements of the array. For example, the array is formed as a linear array with composite elements and kerfs. The backing material is flexible or deformable. The linear array is twisted by any amount. The matching layers and/or electrodes (e.g., flex circuit material) may have sufficient give or be flexible to avoid delaminating by twisting.

The twisted array is held in position by a frame, housing, cured epoxy, guide wires, other structures, or combinations thereof. For example, the array is forced into a corkscrew or helical tool. Epoxy is applied to the array, such as between the flex circuit folds on the back of the array. After the epoxy cures, the epoxy maintains the array in the helix. As another example, the array is connected with a memory metal. When the array is heated, the memory metal twists the array and maintains the twisted position even after cooling. In another example, a catheter or other probe body is forced through a mandrel to form a twist or includes a twisted frame. Placement of the array in the body twists and holds the array. In one embodiment, a flat array is twisted while in use for volume scanning and flattened for high resolution scanning. For example, the adjustment in twist during use is provided by twisting wire relative to catheter body, a memory alloy, or forcing a twisted beam through a guide in the backing material.

In act 42, an aperture is formed on the array of elements. The aperture is all of the elements or a subset of the elements. Any size aperture may be used. The aperture includes contiguously adjacent elements or is sparse. The aperture is formed by connection of conductors and associated elements to the beamformer. The elements used for transmitting and/or receiving during a given transmit and receive event define the aperture. A different aperture may be used for transmit than for receive.

In act 44, a plane is scanned with the aperture. Using electronic focus, transmit and receive beams are formed using the elements of the aperture. By changing the focus, a planar region may be scanned sequentially using the aperture. Single or multiple beams may be formed for transmit and/or receive operations for each event. Plane wave, diverging wavefront, or unfocused transmission may be used. Different apertures may be used for transmit and receive operations. The scanned plane may include a twist or distortion in spatial position due to the twist of the elements within the aperture. In response to the transmission and reception with the aperture, data representing the scanned region is acquired. The rotation of the elements results in the acquired data representing the region at a particular elevation rotation.

In one embodiment, the scan is from a catheter. The scan may be from other transducer probes, such as handheld probes or TEE probes.

Figure 5:
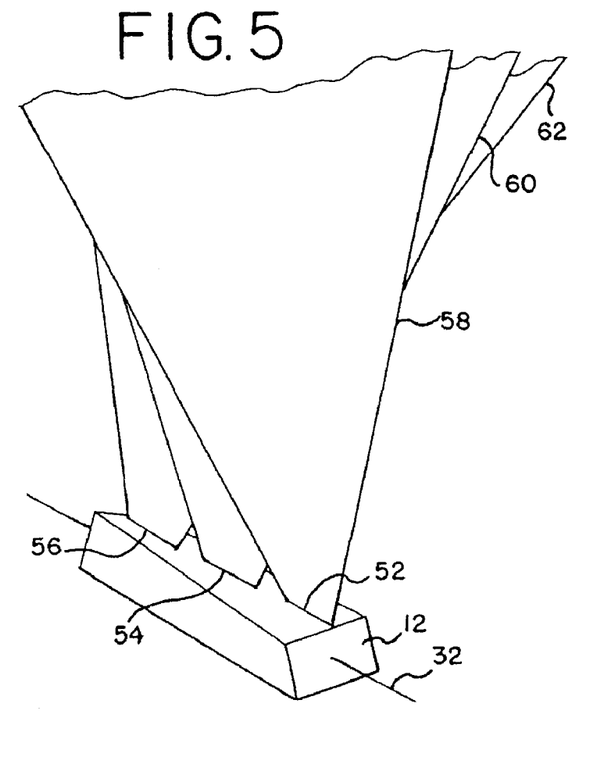
FIG. 5 is a graphical representation showing the scan locations adjacent to the array of FIG. 4.

FIGS. 4 and 5 show the array 12 in a spiral pattern with corresponding apertures 52, 54, 56. For each of the apertures 52, 54, 56, a corresponding generally planar scan region 58, 60, 62, respectively, is scanned. The scan regions 58, 60, 62 are offset from each other in the elevation dimension and are associated with different amounts of rotation about the azimuth axis 32. The planes are adjacent to each other along a dimension substantially orthogonal to the planes (e.g., the elevation dimension). The longitudinal (azimuth) and depth (range) extent of each scan region is similar, overlapping, or different. The elevation angle of each plane is different, such as diverging from a common axis also being the axis of rotation of the array. The intersection of the planes is not in the scanned volume, but instead on or behind the face of the array. In other embodiments, the scan planes may intersect above the array face. Acts 42 and 44 correspond to selecting an aperture and scanning the region associated with the aperture.

In acts 46 and 48, another aperture is formed and the associated region is scanned. By selecting a different aperture, a different plane is scanned. The position of the plane corresponds to a different angle of twist associated with the elements than for other apertures. Other apertures may be formed for scanning other regions or planes. As shown in FIGS. 4 and 5, the planes are spaced apart, but overlap in azimuth and range. No overlap in azimuth and/or range is provided in other embodiments.

In act 50, a three-dimensional representation is generated. The data obtained from the scan is formatted for rendering. For example, the data is interpolated to a three-dimensional evenly spaced grid. As another example, the data for each plane or scan is scan converted into a two-dimensional data set. The two-dimensional data sets associated with each plane are provided for rendering. In another example, the data is maintained in an acquisition format, such as a polar coordinate format. The known plane positions, sample depth, and scan line position provide relative spatial positioning information for each datum.

The data or associated spatial positions may be warped or adjusted to account for planar skew due to the twisting of each aperture. Since the scan region or plane used to acquire data may bend due to the twist or variation in sensitivity as a function of scan line location, the data may be increased or decreased in amplitude. Interpolation may be used between planes to account for spatial offset. Other warping or adjustments may be used.

The three-dimensional representation is rendered as a function of the data from the scanning. The relative positions of the scan planes are used to format the data and/or for rendering. Any now known or later developed rendering may be used. For example, using either view based diverging lines or parallel lines along a viewing direction, projection rendering is provided. Minimum, maximum, first value over a threshold, average, alpha blending or other projection techniques may be used. Surface rendering may be used. Opacity, shading, or other rendering refinements may be applied.

The result of the rendering is a three-dimensional representation from a given viewing direction. The rendering may be performed from another viewing direction with a same set of data. For real-time imaging, the viewing direction may change for subsequently acquired data sets. Real-time three-dimensional imaging may be provided. The three-dimensional representation is an ultrasound image. The data is B-mode, intensity, Doppler mode, velocity, energy, harmonic mode, contrast agent, combinations thereof, or other types of ultrasound data.

Using the three-dimensional representation, tissue structure adjacent the array may be viewed. In the catheter or TEE embodiment, tissue structure of one chamber may be viewed from another chamber or the same chamber. Given the aperture spacing, the near views may provide less volume information for rendering. The array may be positioned a little away from the region to be scanned for higher resolution. The array may be rotated to further increase the volume field of view.

In addition or as an alternative to three-dimensional imaging, two-dimensional images are generated by scanning a single plane or region. Where the array continually twists, the aperture may be limited to scan a single plane. Alternatively, different apertures are used for different scan lines in a twisting plane or region. In other embodiments, a large portion of the array does not twist, so the portion is used for two-dimensional imaging. In yet other embodiments, the array may transition between twisted and non-twisted positions. The array is placed in the non-twisted position for two-dimensional imaging.

Figure 6:
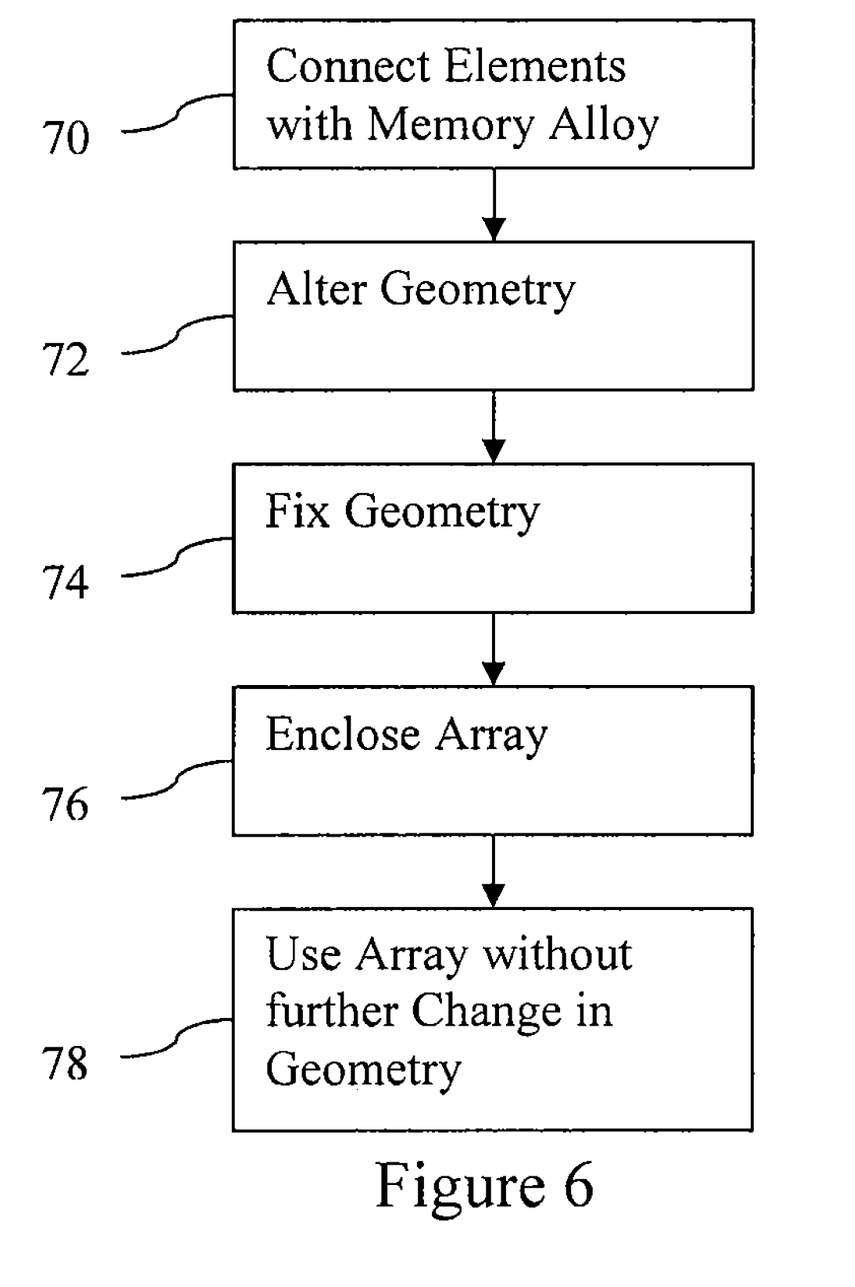
FIG. 6 is a flow chart diagram of one embodiment of a method for manufacturing and using an acoustic array.

In some embodiments, a memory alloy provides the twist, rotation or array geometry. FIG. 6 shows a method for manufacturing an acoustic array with a memory alloy and scanning with the acoustic array. The method uses the system of FIG. 2, the array of FIG. 1, 7-8, or 10, or a different array and/or system. Additional, different, or fewer acts may be provided. For example, the geometry is not fixed in act 74, the array is not enclosed in act 76, and/or the array is not used in act 78.

In act 70, a plurality of ultrasound elements of the array are connected with a memory alloy. The connection may be a clamp or positioning in a fixture. In another embodiment, the elements connect to the memory alloy by bonding, such as with epoxy cured at room temperature or higher temperatures (e.g., 50 degrees Celsius). For example, a memory alloy is stacked with an array and other transducer layers used for an ultrasound transducer (e.g., a backing, a flex circuit with traces, a grounding plane, and/or matching layers). The stack is pressed and cured.

The memory alloy connects with the array directly or through one or more other components. For example, the memory alloy is stacked with an array of matching layer, transducer material, and backing block. Conductors, such as a flexible circuit extend from between the transducer material and the backing block. Excess flexible circuit material is positioned behind the backing block. The alloy is stacked directly against the backing block or against the excess flexible circuit material behind the backing block.

Figure 7:
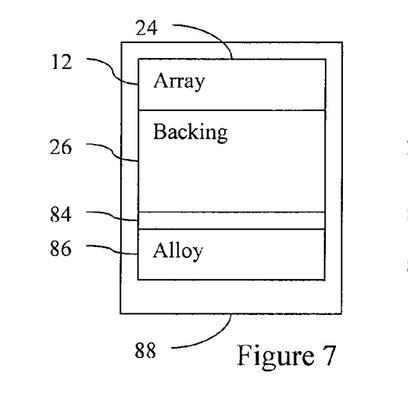
FIGS. 7-8 and 10 are cross-sectional views of different embodiments of a transducer array with memory alloy.

FIG. 7 shows one embodiment of a memory alloy 86 connected with an array 12 through a backing material 26 and one or more layers of conductors 84, such as an accordioned stack of flexible circuit material pressed together. The array 12 is a stack of transducer material with or without any matching layers and conductors. In other embodiments, the array 12 is only transducer material. The alloy 86 is below the array 12, below the backing material 26, and below the conductors 84. The conductors 84 extend from the array 12 (e.g., between the transducer material and the backing) to behind the backing 26. An enclosure 88 encloses the array 12 of elements 24. The layers are connected by bonding. The enclosure 88 connects with, rests against, or is spaced around the stack of the array 12.

Figure 8:
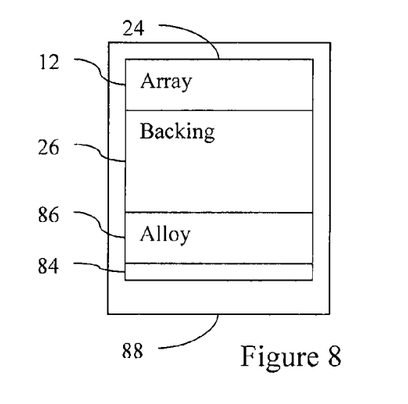

FIG. 8 shows an interconnected stack similar to FIG. 7, but with the memory alloy 86 between the backing 26 and the conductors 84. Other arrangements may be used.

Figure 10:
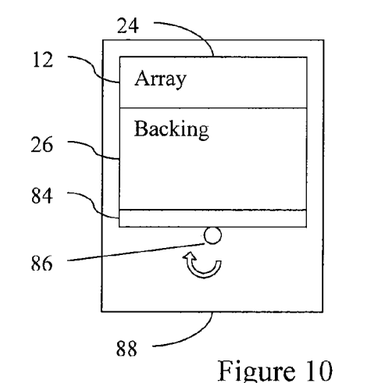

FIG. 10 shows the memory alloy 86 as a rod or tube rather than a sheet or plate of FIGS. 7 and 8. Other shapes and extents along any dimension may be used. In an alternative embodiment, the rod is flat on the side adjacent the array, but cylindrical on the bottom side (i.e., side away from the array 12). The cross-sectional area adjacent to the backing 26 is maximized.

Figures 11, 12:
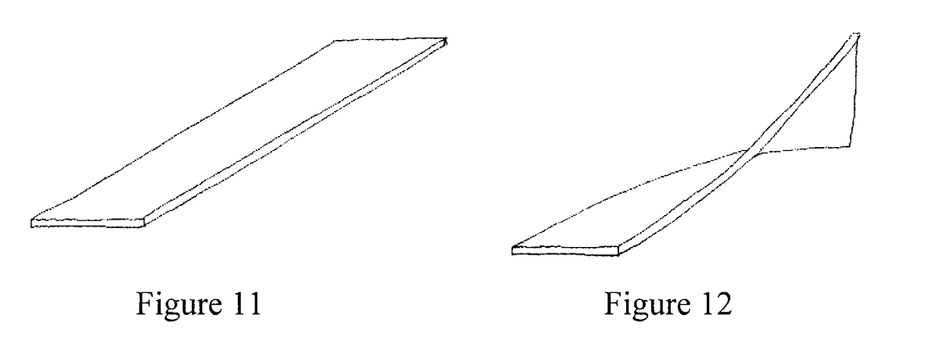
FIGS. 11 and 12 are graphical representations of one embodiment of a sheet of memory alloy in two different positions.

FIG. 11 shows the memory alloy 86 as a flat plate structure, such as associated with the memory alloy 86 shown in FIGS. 7 and 8, prior to heat activation.

In act 72 of FIG. 6, the geometry of the array is altered. The memory alloy alters the geometry during manufacture of a transducer probe including the array. The alloy alters the array to a desired geometry. Any geometry may be remembered by the memory alloy. For example, the desired geometry is flat or planar. As another example, the desired geometry is curved along one or more dimensions (e.g., curved along an azimuth dimension and not along an elevation dimension). In another embodiment, the desired geometry is a helical shape for the emitting face of the array.

The alteration occurs during manufacturing. For example, the alteration occurs after connecting the array to the memory alloy, but before shipping a completed array to customers. As another example, the alteration occurs due to the connection of the memory alloy to the array. The array is altered to connect with the memory alloy. In one embodiment, the array is altered by the memory alloy after connection and prior to or during enclosing the array within a housing.

In one embodiment, the array is altered back to a desired geometry with a superelastic alloy. For example, the array is twisted, bent, warped, or shifted by handling during manufacture. The memory alloy retains the desired geometry, so deforms the array back to the desired geometry. A superelastic alloy sheet, wire, or other shape is affixed to the ultrasound array 12, such as shown in FIGS. 7-8 and 10. The superelastic alloy 86 maintains the planar or other desired geometric surface of the acoustic array 12. In some ultrasound catheter or TEE applications, the backing block of array 12, and/or other material may be thin due to size constraints. Accordingly, the dimensional stability of the transducer stack is less than otherwise could be provided. A larger number of elements may be desired, increasing a lateral (e.g., azimuth and/or elevation) extent of the array. The increased lateral extent may allow for a more easily deformed array 12. Any unwanted deformation of the array during normal manufacturing is reversed by the superelastic alloy component to the acoustic array.

The reversal is alternatively provided by a shape-memory alloy. Rather than automatically returning to the desired geometry, a temperature or other transition of the memory alloy returns or alters the array 12 to a desired geometry.

Figure 9:
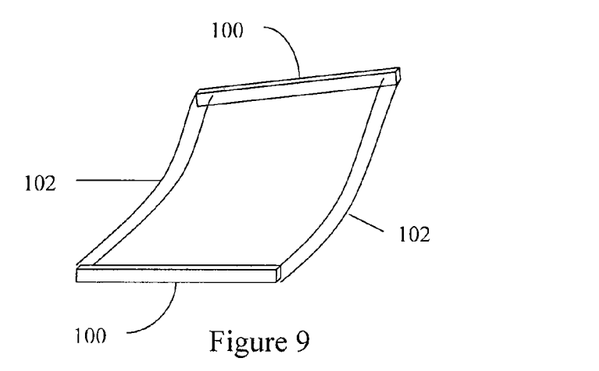
FIG. 9 is a perspective view of one embodiment of a memory alloy frame for manufacturing a transducer array.

FIG. 9 shows another use of superelastic alloy to alter the geometry of an array. A fixture includes superelastic alloy rods 102. For example, two superelastic rods 102 attach to two end pockets 100 of the same or different material. The superelastic rods 102 are bent to insert the array 12 into the two end pockets 100. The superelastic rods 102 then unbend or bend differently due to the memory and force the array 12 to assume the desired geometry.

In one embodiment, the array 12 is altered from one shape to another shape by the memory alloy 86. The memory alloy 86 is forced to transition to a memory state different than a prior state.

Heat or other transition energy causes the alloy to alter the array geometry. For example, a shape-memory alloy, such as Nitinol, is heated. The heat is applied externally to the transducer stack and/or transducer probe. For example, heat applied to plastic weld or form a housing around the transducer stack also causes the memory alloy 86 to transition to a different geometry. Alternatively, heat may be applied internally to a transducer probe, such as by a heating element within a transducer housing and adjacent to the memory alloy 86.

In one example alteration, the memory alloy 86 has a substantially planar shape prior to altering and alters to a curved or helical shape. FIG. 11 shows a sheet of memory alloy 86 with a substantially flat geometry (prior to bonding to the array). After transition, FIG. 12 shows the memory alloy 86 with a helical shape (after plastic welding the array within the enclosure). The elements 24 of the array 12 are twisted about a longitudinal axis of the array (i.e., the azimuth axis). The array 12 is twisted into a helix or spiral around the longitudinal axis. The twisting provides rotation of the ends of the array, and/or rotation of elements or groups of elements of the array. For example, the array is formed as a linear array with composite elements and kerfs. The kerfs may or may not extend into the memory alloy 86 or be formed prior to connection of the array 12 to the memory alloy 86.

The linear array is twisted by any amount. The matching layers and/or electrodes (e.g., flex circuit material) may have sufficient give or be flexible to avoid delaminating by twisting. The backing block is flexible, such as being silicone and/or epoxy with or without fillers. The backing may be other materials and/or thinned for flexibility (e.g., 0.05-0.02 inches thick).

A shape-memory alloy sheet, wire, or other shape affixed to the back of an ultrasound array 12 alters the geometry of the array 12. For example, FIG. 10 shows a shape memory rod 86 epoxy-bonded to the back of the backing material 26. For a subsequent catheter or TEE manufacturing, plastic welding or other heat application is performed. For example, a PET sheet with or without adhesive (PSA) is shrunk or welded around the transducer stack. As another example, a Pebax outer housing forming the catheter encloses the transducer stack by application of heat. During a plastic-welding or other heat application step, the shape-memory alloy 86 reverts to an original or memorized shape, such as the helical shape of FIG. 12. In the example of FIG. 10, the rod twists. Due to the application of heat, the thermoplastic covering 88 of the array 12 is soft enough that the array 12 can assume the geometry defined by the shape-memory alloy 86. A tip (enclosure) of a catheter may be easier to fabricate with a rectangular untwisted lumen. If the array is twisted prior to insertion, then a twisted rectangular tip lumen may be used to insert the array into the tip.

In a further embodiment, the shape-memory alloy 86 provides a frame, such as shown in FIG. 9. A combination of fixturing and stacking may be provided for further stability. For example, a sheet of Nitinol is stacked in the transducer stack. A thin wall of the sheet is bent upwards to cover a portion or entire side or sides of the transducer stack. The side walls morph differently than the stacked portion to provide a Nitinol cylinder or fixture. Thinner Nitinol may be used in the stack due to the added stability, minimizing the size of the transducer stack.

For shape memory alloy, the transformation occurs at a desired temperature. Any temperature above room and/or above likely body temperatures may be used. For example, the memory alloy 86 does not transition below 50 degrees Celsius. The stack is bonded at 50 degrees Celsius or less. The transition temperature is below another manufacturing temperature, such as below the plastic welding temperature. In the case of low-durometer Pebax, the transformation occurs at a temperature below 140 degrees Centigrade. Other temperatures may be used. Separate application of heat may be used. For example, the transition does not occur during plastic welding, but occurs at another temperature applied only for transition or applied for other purposes to form the transducer probe.

In act 74, the geometry of the array 12 is fixed after the altering. The alteration sets the desired geometry during manufacture. The geometry remains the same for all subsequent use. For example, the array 12 is used in a catheter 11 as shown in FIG. 2. After fixing the geometry during manufacture, the array 12 maintains a same geometry for shipping, preparing for scanning, insertion within a patient, and/or scanning. Changes in geometry due to stress or strain may occur, but intentional changes in geometry are not provided. In alternative embodiments, the geometry of the array 12 is subsequently altered. For example, a desired shape is maintained or provided during manufacture. Structure, a hinge, other memory alloy, or other device is provided for altering the geometry during use (e.g., transitioning from a flat or a helical geometry or vise versa).

The geometry of the array 12 is held in position by a frame, housing, cured epoxy, guide wires, other structures, the memory alloy 86, or combinations thereof. For example, the memory alloy 86 alters the shape of the array 12. Material may be added to the stack and bonded with the array 12 or other material to maintain the array 12 in the desired geometry. The array 12 can then be fixed in place with an adhesive and the fixture removed. Alternatively, the fixture can be left in place, as the fixture is completely outside the acoustic path.

The memory alloy 86 remains in the stack or is removed. For example, the memory alloy 86 is on an emitting face side of the array 12. Bonding of the housing 88, bonding of the transducer stack, or added material bound to the transducer stack is added to the array 12 in the desired position. The memory alloy 86 is removed by debonding or lapping. Alternatively, the memory alloy 86 acts as a matching layer or is positioned behind the array 12.

In act 76, the array 12 is enclosed by a housing 88. The array 12 is enclosed by a protective material, such as a film of electrically insulating material. In one embodiment, the array 12 is enclosed in a transducer probe housing, such as a plastic housing for handheld use. The array 12 may be enclosed in a catheter, TEE or other housing. The enclosure is a clamshell, shrink-wrap, or other housing. For example, plastic welding encloses thermoplastic around at least a portion of the array 12. Epoxy or other bonding agent may be provided between the housing 88 and the array 12. Multiple layers of housing material may be used, such as one layer for electrical insulation and another for the outer surface of the probe.

In act 78, the array 12 is used without a change in geometry. Linear, sector, Vector® or other ultrasound scan formats may be used. In one embodiment, the array 12 has a helical geometry. The elements 24 of the array 12 are used to provide sequentially different imaging plane positions. The imaging plane from one portion of the array will face a different direction than another portion of the array. The array 12 has a fixed position, but may be altered during or for scanning.

Any now known or later developed memory alloy may be used. For example, a shape-memory alloy is used, such as Nitinol. The shape-memory alloy has a current shape and a remembered shape. Upon application of energy, such as heat, the shape-memory alloy returns from the current shape to the remembered shape. The transition alters the emitting face 22 of the array 12. For example, the emitting face 22 is altered from a substantially planar geometry to a fixed, non-planar geometry.

Another example memory alloy 86 is a superelastic alloy. Superelastic alloys may be bent, twisted or otherwise altered, but return to a remembered shape or geometry. For example, the superelastic alloy returns the emitting face 22 of the array 12 to a desired geometry after any distortion. The desired geometry may be fixed at the conclusion of manufacturing.

The memory alloy 86 may be connected in any manner with the array 12 to provide the desired influence. For example, the memory alloy 86 is stacked with the array 12 along a range dimension as shown in FIGS. 7-8 and 10. The range dimension is substantially orthogonal to the emitting face 22 at a given location. The sheet of memory alloy 86 has a substantially same azimuth and elevation extent as the array 12, but may be smaller or larger. As another example, the memory alloy 86 is part of a frame, such as shown in FIG. 9.

The elements 24 are held in place or altered to return to a desired geometry by the memory alloy 86. During manufacture, additional material may be added to hold the elements 24 at a geometry established by the memory alloy 86. The additional material, the memory alloy 86, or both fix the position, such as permanently, for later use. For example, the enclosure 88 (e.g., Pebax) is premolded to be a close fit between the array 12 and flex connection bundle 84. When the enclosure 88 is melted, the array 12 is twisted by the alloy and all open spaces are filled with material from the enclosure 88 or epoxy added within the enclosure 88. Upon curing, the elements 24 are held in position. As another example, a frame holds the elements 24 in place. In another example, epoxy or other bonding agent cures against a portion or the entire array 12 to hold the array 12 in position. Other materials and associated structures may be used. For the catheter embodiment, the body of the catheter 11 may twist or rotate to avoid interference with, hold in place, or assist in holding in place the rotated elements 24.

The backing block material, electrodes, ground plane, and/or matching layers are deformable, allowing twisting with the elements 24. For example, an array 12 normally used as a linear array may be twisted without further changes in manufacture processes. Alternatively, one or more of these layers are formed after alteration to avoid deformation.

In one embodiment, flex circuit resides between the backing block and the PZT. The flex circuit bends around the side of the backing block and is folded (in an accordion fashion) behind backing block. Within the flex connection bundle (accordion) 84, the flex circuit is connected to the bundle of conductors 14 that transmit the signals between the beamformer 16 and the array 12. In one variation, the flex connection bundle 14 resides between the backing block and the alloy 86 (see FIG. 7). In another variation, the alloy 86 is positioned between the backing block and the flex connection bundle 14 (see FIG. 8).

A transducer with arrays having different geometries may be provided. For example, different groups of elements are twisted or rotated differently. The different elements may be adjacent each other. For example, two or more arrays are substantially parallel. Substantially may account for non-linear axes of one or more arrays and/or other differences caused by the difference in array rotation along the axis of the array. The arrays are aligned to allow scanning of a greater range of planes or larger volume. One array may scan over a 21 degree field, and another array may scan over a different 21 degree field for scanning 42 degrees through a volume. Other ranges may be provided.

FIG. 13 shows the shape memory alloy for four substantially parallel arrays with different geometries. Fewer or more arrays may be used. In the embodiment of FIG. 13, every other array is rotated in a same direction such that two arrays rotate oppositely from two other arrays. Each array is rotated oppositely from the adjacent arrays. The same amount of rotation or different amounts of rotation may be used for each array. All the arrays may be rotated in a same direction. The same or different array structure, such as groupings of elements in each rotation increment, number of elements, length of array, type of elements, or element size, is provided for each array.

The arrays are adjacent to each other. As shown in FIG. 13, the arrays and/or the memory alloy may be connected. For example, the shape memory alloy is connected at alternative ends of arrays, providing rigid relative positioning of the arrays. The connected ends may be flat (e.g., have an emitting face aimed in the same direction) or not flat across the connected arrays. The emitting faces at the connected ends may be aimed to overlap scan region (e.g., emitting faces angled toward each other) or to further separate scanned regions (e.g., emitting faces aimed away from each other). Overlapping may allow for data-based correlation registration or confirming of proper relative positioning of the arrays. Alternatively, one or more of the arrays are spaced from others of the arrays.

The arrays are angled to scan different regions with or without overlap. The relative position and array geometry define different regions to be scanned, such as shown in FIGS. 4 and 5 for one array. The other array or arrays may be used for the same type of scanning, but at different relative positions. In one embodiment, the four arrays cover about 84 degrees where each array covers 21 degrees. The coverage of each array is based on the aperture selection along the array.

In alternative embodiments, the arrays are non-parallel, such as being positioned with generally orthogonal axes. Any arrangement of two or more twisted arrays may be provided.

During manufacture of the array, the memory alloy is flat. The memory alloy may include cuts separating the different arrays, at least partially. Alternatively, the alloy is cut during array manufacture. The element dicing between arrays may be through all of or most of the backing block. Once the array is diced, the memory allow may twist the arrays to the desired geometry. One or more of the arrays may be untwisted. In the embodiment of FIG. 13, the first and third arrays have right hand twist and the second and fourth arrays have left hand twist.

For two arrays adjacent to each other, the flex circuit or conductors may be routed to the exposed sides of each array away from the other arrays. For three or more adjacent arrays, one or more arrays may have both sides near or against another array. A shared flexible circuit may be used. Where insufficient room for traces from two arrays is provided on one side of the flexible circuit, a multi-layer flex may be used. For example, the traces from one array are routed on one side of the flex material. The flex material contacts multiple arrays. The traces for the other array are routed to the other side of the flex material. Other signal routing may be used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system having an acoustic transducer, the system comprising:
    a first plurality of first elements of a first array defining a first emitting face of the first array, the first elements spaced along an azimuth axis, some first elements of the first array rotated about the azimuth axis in a twisted relationship, relative to other first elements, the first emitting face angled in different directions based on the rotation;
    a second plurality of second elements of a second array defining a second emitting face of the second array, the second elements spaced along an azimuth axis, some second elements of the second array rotated about the azimuth axis in a twisted relationship, relative to other second elements, the second emitting face angled in different directions based on the rotation; and
    electrical conductors connected with respective first and second elements;
    wherein the first and second arrays are rotated about the azimuth axis in opposite directions such that the twisted relationship of the first elements to each other is opposite the twisted relationship of the second elements to each other.

2. The system of claim 1 wherein the first elements are rotated about the azimuth axis in a first helical pattern, and wherein the emitting face is twisted based on the rotation, and wherein the second elements are rotated about the azimuth axis in a second helical pattern, and wherein the emitting face is twisted based on the rotation.

3. The system of claim 1 wherein elements at opposite ends of the first array are rotated about the azimuth axis by at least 10 degrees relative to each other, the first emitting face also being rotated about the azimuth axis by at least 10 degrees.

4. The system of claim 1 wherein the first plurality includes at least fifty first elements along the azimuth axis, each of the first elements rotated relative to at least one adjacent element.

5. The system of claim 1 wherein the conductors for each of the first and second elements are addressable as a single array.

6. The system of claim 1 further comprising:
memory alloy operable to hold the first and second elements at the rotated positions.

7. The system of claim 1 further comprising:
a transesophageal probe;
wherein the first and second arrays are positioned within the probe with the first and second elements in the rotated positions.

8. The system of claim 1 further comprising:
a beamformer connected with the conductors, the beamformer configured to scan from a plurality of apertures formed by adjacent groups of the first and second elements; and
a processor configured to generate a three-dimensional data set as a function of the scanning by the beamformer.

9. The system of claim 1 wherein the first and second arrays connect adjacent first and second ends, respectively.

10. The system of claim 1 further comprising:
third and fourth arrays connected with the first and second arrays, the third and fourth arrays rotated in a twisted relationship, the first, second, third, and fourth arrays rotated in opposite directions from adjacent ones of the first, second, third and fourth arrays.

11. In a method for scanning with a medical ultrasound transducer having elements, the scanning comprising steering acoustic energy along a plane with the elements of the transducer, an improvement comprising:
scanning different planar regions stacked in elevation and having similar azimuth extent from the elements arranged in at least two helices such that different groups of at least one element per group spaced along the azimuth axis of each of the at least two helices are operable to scan the different planar regions and such that different ones of the planar regions are scanned using different ones of the at least two helices.

12. The improvement of claim 11 wherein scanning comprises scanning with the elements of each helix defining an emitting face of the transducer, each emitting face angled in different directions based on the helix.

13. The improvement of claim 11 wherein scanning comprises scanning with elements at opposite ends of each helix of the transducer being rotated about the azimuth axis by at least 10 degrees relative to each other.

14. The improvement of claim 11 wherein scanning comprises scanning with each of the elements having substantially wavelength or less spacing in azimuth; and
further comprising positioning the elements in the helices with a memory alloy.

15. The improvement of claim 14 wherein the helices are substantially parallel arrays with a single piece of memory alloy supporting both helices.

16. The improvement of claim 11 wherein scanning comprises scanning with the transducer comprising a transesophageal transducer.

17. The improvement of claim 11 wherein scanning comprises scanning with the at least two helices comprising at least three helices.

18. A method for scanning with an acoustic transducer, the method comprising the acts of:
forming a first aperture on a first array of elements, the first array of elements twisted about a first longitudinal axis;
scanning a first plane with the first aperture;
forming a second, different aperture on the first array of elements, the second aperture corresponding to walking the first aperture azimuthally along the first array of elements, the elements of the first array being along a same line defined by the elements being twisted about the first longitudinal axis;
scanning a second, different plane with the second aperture, the position of the second plane corresponding to a different angle of twist associated with the elements of the first aperture than the elements of the second aperture;
repeating the forming acts and scanning acts with a second array of elements twisted about a second longitudinal axis, wherein the repeating is for third and fourth planes different than the first and second planes, wherein the scanning of the first, second, third, and fourth planes occurs with the first and second arrays being held in a same twisted position; and
generating a three-dimensional representation as a function of data from the scanning and the relative positions of the first, second, third, and fourth planes.

19. The method of claim 18 wherein the second and fourth planes are adjacent to and non-coplanar with the first and third planes, respectively, a longitudinal and depth extent of the scans of the first, second, third and fourth planes being substantially similar.

20. The method of claim 18 wherein the scanning acts comprise scanning from a transesophageal probe.

* * * * *